United States Patent [19]

Updike et al.

[11] Patent Number: 4,568,335
[45] Date of Patent: Feb. 4, 1986

[54] DEVICE FOR THE CONTROLLED INFUSION OF MEDICATIONS

[75] Inventors: Stuart J. Updike; Mark C. Shults, both of Madison, Wis.

[73] Assignee: Markwell Medical Institute, Inc., Madison, Wis.

[21] Appl. No.: 415,757

[22] Filed: Sep. 7, 1982

Related U.S. Application Data

[63] Continuation-in-part of Ser. No. 297,369, Aug. 28, 1981, abandoned, which is a continuation-in-part of Ser. No. 177,892, Aug. 14, 1980, abandoned.

[51] Int. Cl.[4] .............................................. A61M 5/30
[52] U.S. Cl. ..................................... 604/211; 604/224
[58] Field of Search ................ 604/208, 211, 218, 224

[56] References Cited

U.S. PATENT DOCUMENTS

| 951,160 | 3/1910 | Wainwright | 604/224 |
|---|---|---|---|
| 2,250,467 | 7/1941 | Cole | 604/211 |
| 2,660,342 | 11/1953 | Ruf | 604/211 X |
| 3,734,079 | 5/1973 | Weber | |
| 4,189,065 | 2/1980 | Herold | 604/211 X |
| 4,312,343 | 1/1982 | LeVeen et al. | 604/211 |
| 4,367,739 | 1/1983 | LeVeen et al. | 604/224 |
| 4,498,904 | 2/1985 | Turner et al. | 604/211 |

Primary Examiner—Dalton L. Truluck
Attorney, Agent, or Firm—Dressler, Goldsmith, Shore, Sutker & Milnamow, Ltd.

[57] ABSTRACT

A device comprising a container and a threaded rotatable plunger mechanism including means for controllably advancing the plunger through the container can administer a precise dose of a drug-containing fluid subcutaneously at regular intervals. The means for controllably advancing the plunger comprises a drive tube concentrically mounted about a threaded rod operating within the container, the drive tube having ramp means at the upper end thereof, a ratchet head including a resilient member in operative communication with the upper end of the drive tube and a rotatable knob adjacent the ratchet head whereby rotation of the knob in one direction rotates the drive tube and the threaded rod to deliver the fluid through an outlet of the container.

22 Claims, 13 Drawing Figures

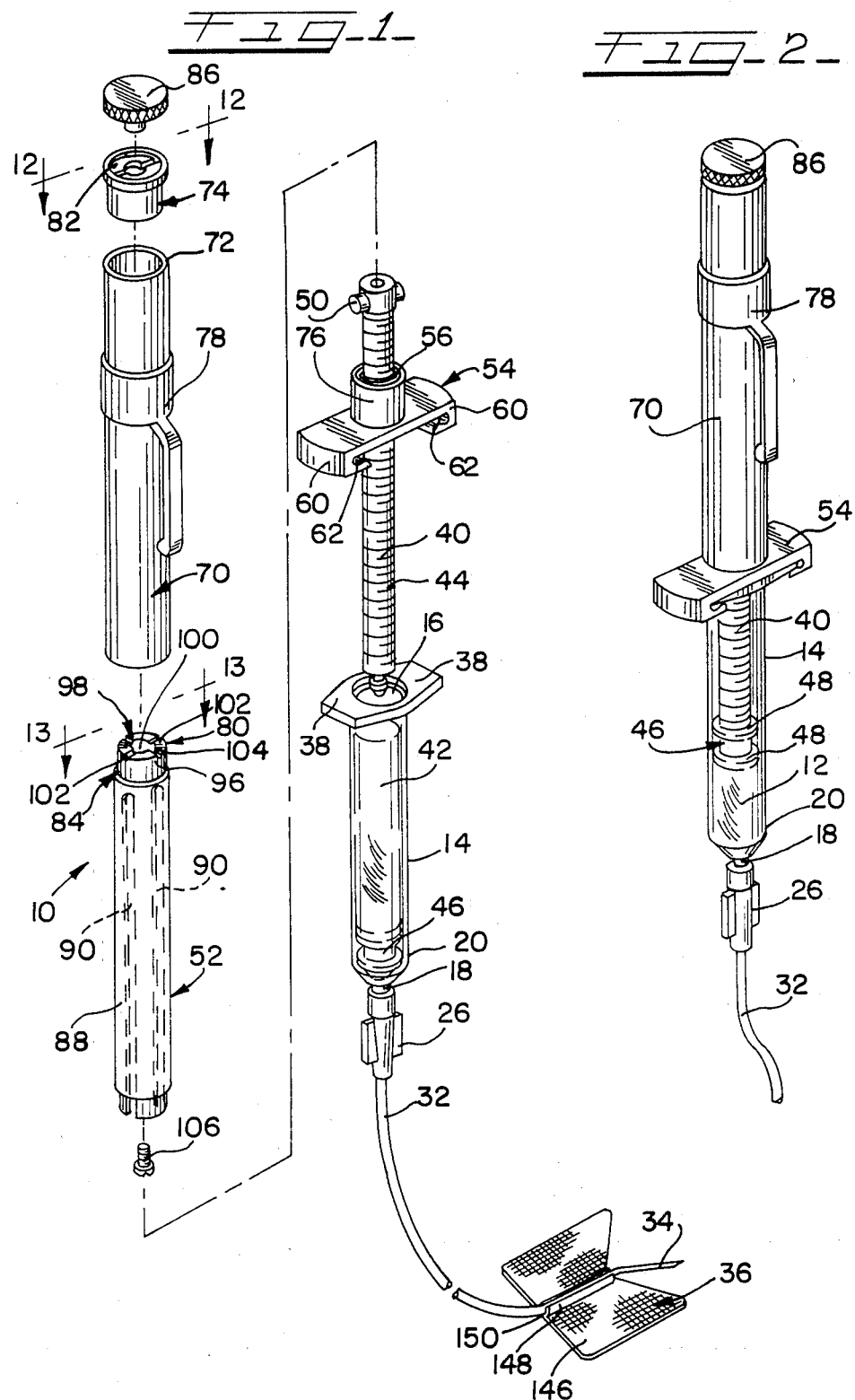

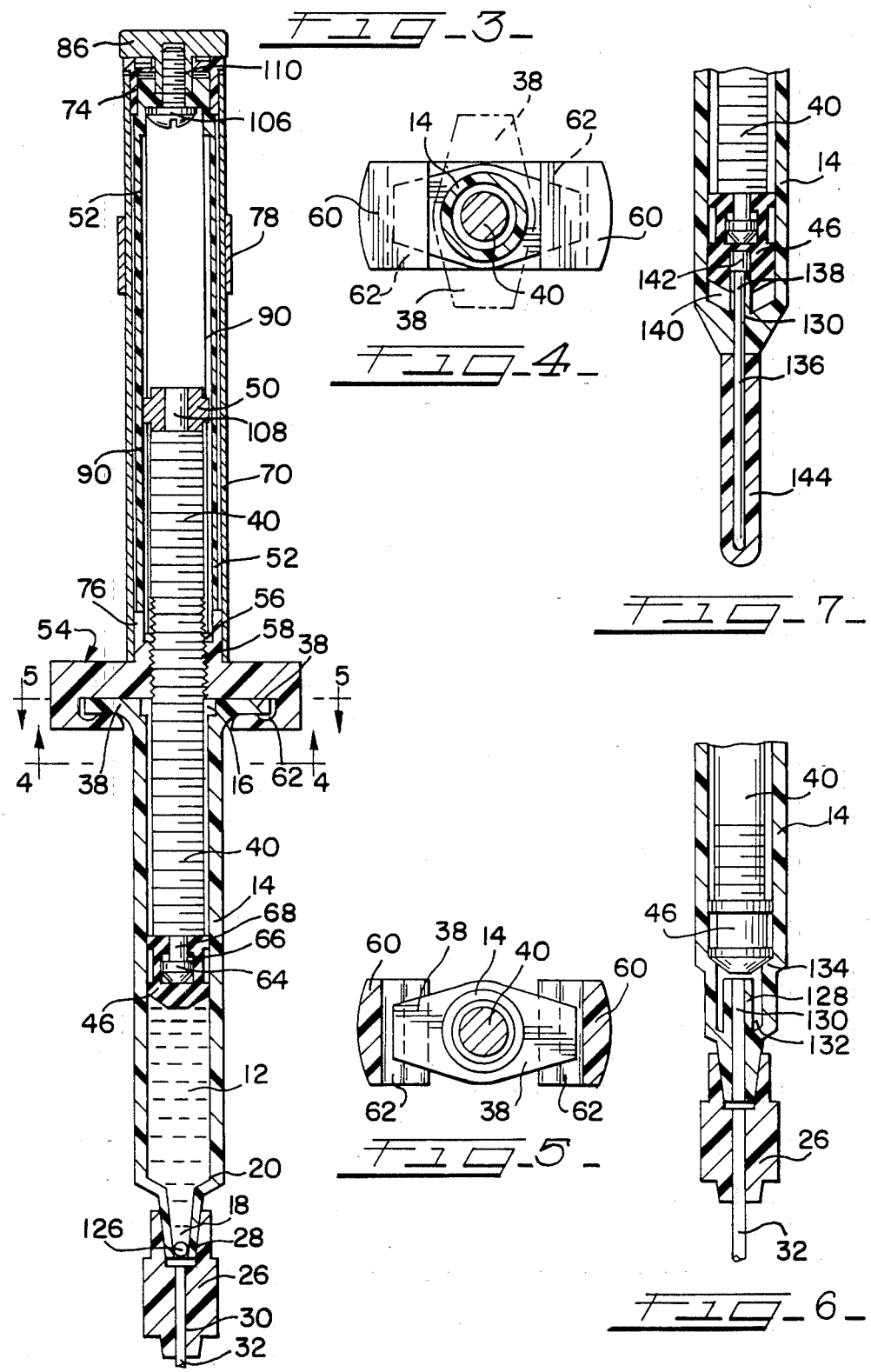

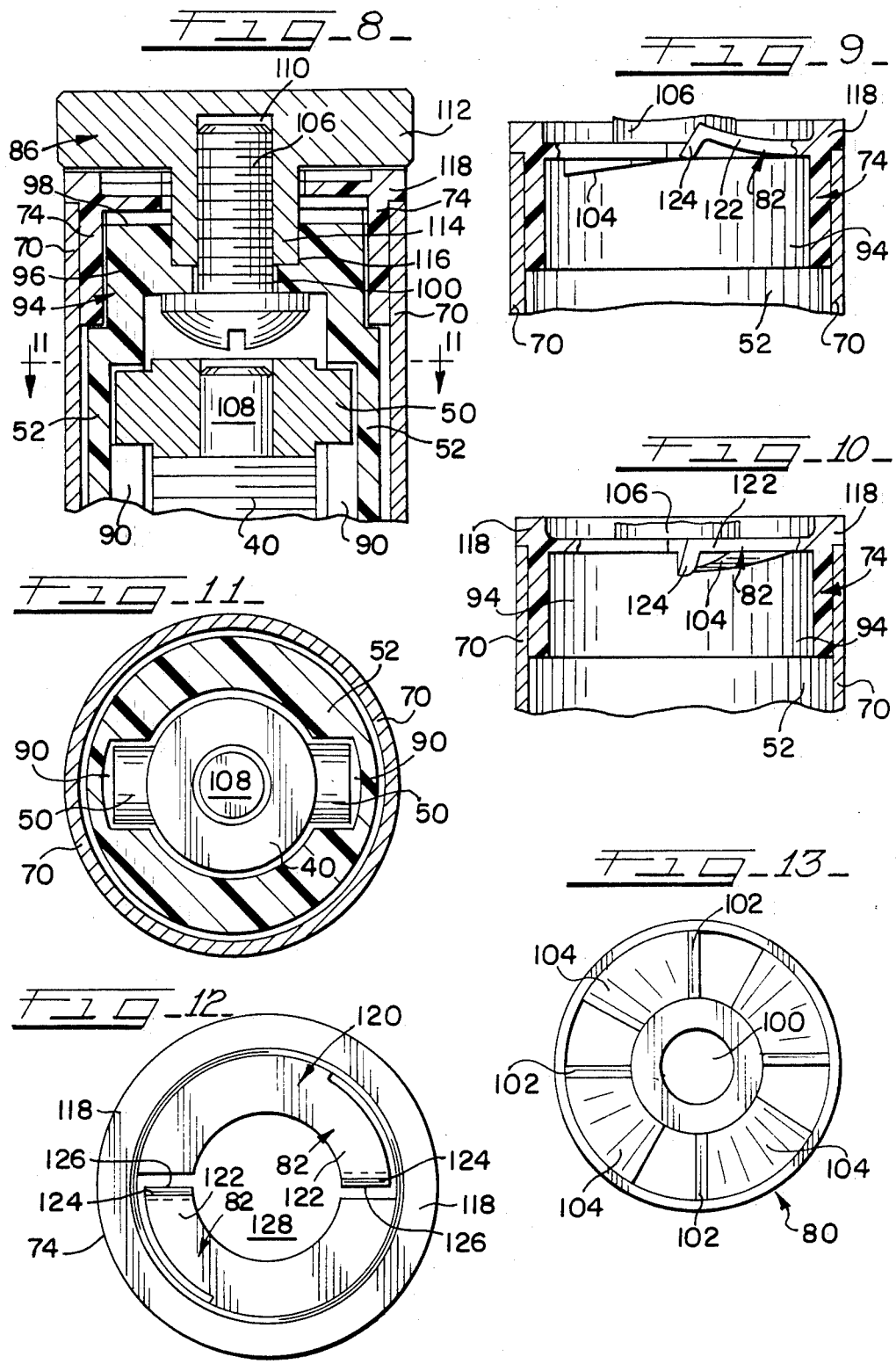

DEVICE FOR THE CONTROLLED INFUSION OF MEDICATIONS

CROSS REFERENCE TO RELATED APPLICATIONS

This application is a continuation-in-part of our copending application Ser. No. 297,369 filed Aug. 28, 1981, now abandoned, which in turn is a continuation-in-part of our copending application Ser. No. 177,892, filed Aug. 14, 1980, now abandoned, both entitled "Device For The Controlled Infusion Of Medications."

BACKGROUND OF THE INVENTION

The present invention and our copending applications relate generally to devices for the controlled infusion of medications and specifically, to devices for the administration of a precise dose of a drug-containing fluid. The devices have particular applicability in the subcutaneous delivery of insulin to a diabetic patient so that blood glucose levels can be normalized. The devices can also be used, under the supervision of a physician, to administer cancer chemotherapuetics, antibiotics, heparin and many other pharmacological agents.

Insulin is used primarily in the control of the metabolic disturbance of diabetes mellitus when that disease cannot be satisfactorily controlled by diet alone. This hormone is secreted by the cells of the island of Langerhans in the pancreas and regulates the rate at which the body metabilizes carbohydrates. Insulin, in appropriate doses, enables the diabetic to utilize carbohydrates and fats in a comparatively satisfactory manner so that the concentration of sugar in the blood is confined within normal limits; the urine becomes free of sugar and ketone bodies; and diabetic acidosis and coma are prevented.

The hormone is prepared commercially by extraction from beef and pork pancreas. Various insulin preparations, which differ in rapidity of action and duration of effectiveness, are used in the treatment of diabetes mellitus. Regular insulin is effective almost immediately upon injection and reaches its peak of action within two hours. It is used in diabetic emergencies and when diabetes is first diagnosed. Moreover, regular insulin is often mixed with longer acting forms of insulin for subcutaneous injection as part of the long term management of diabetes.

Other types of insulin developed in recent years are formulated to prolong the action of insulin. Protamine zinc insulin (PAI), isophane insulin (NPH), globin zinc insulin and lente insulin are examples of long-acting insulin preparations. All insulin preparations, however, have the same fundamental pharmacologic action.

In protamine zinc, isophane and lente insulin, the active material is present as a milky-white precipitate and not a clear supernatant fluid. To insure that a constant proportion of this precipitate is present in each dose injected, the vial must be rotated and inverted from end to end several times immediately before the withdrawal of each dose. A failure to observe this procedure can lead to a marked irregularity in the effects of individual doses. The vial, however, should not be shaken vigorously or the suspension made to foam. Such frothing is avoided primarily because the air bubbles produced can alter the dosage measured in the syringe.

Lente insulin combines approximately 70 percent of ultralente and 30 percent of semilente insulin. Lente, semilente and ultralente insulin represent the result of the interaction of zinc on insulin under specific chemical conditions so that higher concentrations of the metallic element are made to combine with the insulin present. As indicated, they are supplied in the form of a suspension of minute crystalline particles. Semilente insulin has the smaller particle size and the shorter action, with a duration of effect of approximately twelve to sixteen hours. Ultralente insulin has the larger particle size and a total duration of effect in excess of thirty-six hours. Thus, lente insulin has a time action which is intermediate between semilente and ultralente insulin. In fact, the action of lente insulin is so close to that of isophane insulin that the two can be used interchangeably.

Insulin is measured in units based on bioassay, and is commercially available in varying strengths; for example, U-40, U-80 and U-100. The term U-40 means that there are 40 units of insulin per milliliter of solution. When measuring the drug in an insulin syringe, one must be careful to use a syringe calibrated to correspond with the strength of the insulin preparation being used. But regardless of the concentration, the action of insulin is basically the same—to enable carbohydrate metabolism to occur and to prevent the accumulation of excess ketone bodies in the blood.

Hypoglycemia and insulin shock result when the level of insulin in the body is too high. This may be the result of an insulin overdose, failure to eat a full meal at the prescribed time, more than the usual amount of exercise, or an emotional or physical upset. Hypoglycemia, if transient and mild, does not cause disabling symptoms; however, if the blood sugar level remains very low for a prolonged period of time, symptoms of cerebral dysfunction or brain damage develop as the brain is deprived of the glucose needed for its normal metabolic activities. Consequently, insulin shock is an ever present danger to those who must take insulin for diabetes mellitus. In addition, devastating retinal, renal and cardiovascular complications are often suffered by diabetics. Recent human and animal studies have indicated that poor control of blood glucose is a principal cause of these complications.

The need exists, therefore, for a device to control the level of blood glucose in a diabetic patient through the infusion of a precise quantity of insulin so that the long-term microvascular and neuropathic complications of diabetes are avoided, or at least minimized. The device must regularly infuse insulin to mimic the release of insulin by the normal pancreas.

Mechanical devices are available to improve the control of blood glucose by the continuous infusion of insulin at a predetermined basal rate. These wearable devices are preprogrammed to infuse shortacting, noncrystalline, regular insulin. Regular insulin should not be confused with the modified long-acting insulins, such a protamine zinc, isophane, globin zinc and lente insulin.

The wearable devices for continuous insulin infusion are also designed to allow the administration of a bolus or increased infusion of regular insulin before each meal. To achieve the desired basal level of insulin, continuous, or at least frequent, activation of the infusion pump is required. Thus, the infusion pump must be carried or worn by the patient. Unfortunately, the currently available wearable infusion devices are expensive, complex and too bulky to be worn comfortably. Moreover, the complicated electronic and mechanical components can wear out or malfunction, and the batteries of the device must be replaced or recharged at regular intervals.

The complexity of these preprogrammed pumps also raises a safety issue. The patient must switch the infusion pump out of the basal infusion mode to activate the pump to infuse each pre-meal insulin bolus. If the patient inadvertently leaves the pump in the bolus infusion mode instead of immediately switching back to basal infusion, the timer may activate frequent bolus infusions which could lead to lifethreatening hypoglycemia or insulin shock. The invention of our copending application Ser. No. 177,892 is directed to the solution of these problems.

In addition, the operation of pressfitting the rod into the piston member can bend the end of the needle which extends into the container. The device of Ser. No. 297,369 includes an annular ledge or indentation along the inner wall of the container to arrest the motion of the piston member on the downward stroke.

Moreover, the needle for infusing the medication should be contoured to permit proper anchoring of the needle to the skin. A straight needle, when secured to the skin by tape or similar fastening means, has a tendency to pivot with the fastening means which serves as a fulcrum thereby widening the needle track; the passage formed between the needle and the tissue of the patient as the needle is inserted into the skin. The device of Ser. No. 297,369 is also directed to the solution of these additional problems.

The present invention relates to the solution of the aforementioned problems and additional difficulties which may arise in the infusion of insulin. According to the present invention, the plunger can be advanced within the container without removing the cap or cover member. Specifically, means is provided for concentrically advancing the plunger comprising a drive tube concentrically mounted about a threaded rod operating within the container, the drive tube having ramp means at the upper end thereof, a ratchet head including a resilient member in operative communication with the upper end of the drive tube and a rotatable knob adjacent the ratchet head whereby rotation of the knob in one direction rotates the drive tube and the threaded rod to deliver the fluid through an outlet of the container.

Because the fluid is delivered only upon rotation of the knob in a predetermined direction, the device can be used without direct viewing—a distinct click is produced upon rotation of the knob when the resilient member of the ratchet head operatively engages the upper end of the drive tube to indicate the delivery of a given volume of fluid.

SUMMARY OF THE INVENTION

The invention is a device for the controlled infusion of medications. In particular, a precise dose of a drug-containing fluid can be administered subcutaneously, intravenously, or intraperitoneally at regular intervals. Subcutaneous infusion is preferred rather than intravenous or intraperitoneal infusion to minimize the possibility of intravascular thrombosis, infection or peritonitis. The device has particular applicability in the delivery of insulin to a diabetic patient so that blood glucose levels are normalized and the major complications of diabetes mellitus are avoided; but the device can also be used to administer cancer chemotherapeutics, antibiotics, heparin and other pharmacological agents.

The preferred embodiment of the invention includes two concentrically placed members: a container, such as a conventional syringe or a similar cylinder containing a piston member, and an elongated rod threadably fitted within the container that engages the piston member to pump the drug-containing fluid from the container. Means is provided for controllably advancing the plunger comprising a drive tube concentrically mounted about the threaded rod, the drive tube having ramp means at the upper end thereof, a ratchet head including a resilient member in operative communication with the upper end of the drive tube and a rotatable knob adjacent the ratchet head whereby rotation of the knob in one direction rotates the threaded rod to deliver the fluid through an outlet of the container.

In use, the rod is inserted into the container to engage the piston member. When the rod engages the piston member, the rod is concentrically positioned within the container and cannot contact the inner wall. The container is then sealed, and the fluid is drawn into the container. The plunger advancing means is secured to the upper end of the rod to complete the assembly. If insulin is to be administered for example, the fluid can comprise a mixture of between 60 to 80% of U-100 short-acting, regular insulin and between 20 to 40% of U-100 longacting, ultralente insulin in a sufficient volume so that the container holds at least a 24 hour supply of insulin.

As previously indicated, the container must be rotated and inverted from end to end several times immediately before the infusion of each dose to insure a constant proportion of regular and long-acting insulin. This step of resuspending the long-acting insulin crystals is essential for the safe and effective operation of the device. A small stainless steel ball or an air pocket can be provided within the container to facilitate the mixing upon inversion.

Catheter tubing can be attached via an adaptor to the container. The other end of the tubing is then joined to a curved needle which is inserted into the subcutaneous tissue of the abdominal wall, for example, and is secured with tape means so that the device may be worn by the patient. Other sites of infusion include the subcutaneous tissue of the upper arm or thigh, or the intraperitoneal cavity. The container, adaptor, tubing, tape means and needle are disposable and, along with the infusion site, should be changed every one to three days.

After inversion of the container to resuspend the insulin crystals, the knob is manually rotated in one direction through a given arc to deliver the desired quantity of fluid through the tubing and the subcutaneously positioned needle. A screw-thread size of the rod can be selected so that each quarter revolution of the knob infuses exactly one unit of U-100 insulin. Other thread sizes are also contemplated.

In addition to the anticipated low cost of the present invention, this device is less bulky than currently available infusion pumps. The administration of four bolus infusions per day before each meal and at night is sufficient to maintain a relatively constant blood glucose level. The regular insulin acts rapidly to metabolize the carbohydrates ingested at each meal, and the long-acting insulin maintains a baseline insulin in the blood for longer periods of time.

It follows that it is the principal object of this invention to provide a simple device which can be operated to deliver a controlled dose of a medication. The device is inexpensive to manufacture, and the infusion procedure can be performed with minimal instruction. The device is also small enough to be worn comfortably by a patient.

It is an additional object of the invention to minimize the chances of drug overdose due to mechanical or human error. In addition, the failure of a preprogrammed pump resulting in a decreased dose is avoided.

A further object of the invention, when insulin is the drug being administered, is to deliver insulin to a diabetic patient so that blood glucose levels are normalized and the major complications of diabetes mellitus are avoided.

Other objects and advantages will be apparent from the following detailed description made with reference to the accompanying drawings.

BRIEF DESCRIPTION OF THE DRAWINGS

FIG. 1 is an exploded perspective view that illustrates the components of the device;

FIG. 2 is a perspective view of the device of the present invention assembled for use;

FIG. 3 is a sectional view of the device of FIG. 2;

FIG. 4 is a sectional view taken along the line 4—4 of FIG. 3;

FIG. 5 is a sectional view taken along the line 5—5 of FIG. 3;

FIG. 6 is a sectional view of a second embodiment of the device having an alternative configuration of container opening;

FIG. 7 is a sectional view of a third embodiment of the device having an alternative configuration of container opening;

FIG. 8 is a sectional view of the upper portion of the device;

FIGS. 9 and 10 are sectional views of the ratchet head and the drive tube in the released and locked positions, respectively;

FIG. 11 is a sectional view taken along the line 11—11 of FIG. 8;

FIG. 12 is a sectional view taken along the line 12—12 of FIG. 1; and

FIG. 13 is a sectional view taken along the line 13—13 of FIG. 1.

DETAILED DESCRIPTION OF THE INVENTION

FIG. 1 illustrates a device generally designated by the numeral 10 for the controlled infusion of a fluid 12. The fluid, which can include any pharmacological agent, is held in a container 14 having the form of a syringe which is open at the top 16 and is provided with a small outflow channel 18 in the tip portion 20 of decreasing dimension at the bottom 24.

An adaptor 26 is provided with a cavity 28 at one end that corresponds with the external contour of the tip end portion 20 of the container for releasably mounting the adaptor on the tip end portion in a sealing relation. The adaptor is formed with a continuous passage 30 extending therethrough for communication at one end with the outflow channel 18 in the tip of the container while the other end of the passage 30 receives a flexible tubing 32 secured to a hollow injection needle 34 for the subcutaneous infusion of injection of the fluid 12 into a patient. Tape means 36, which will be described, secures the needle 34 to the skin. The infusion site can include the subcutaneous tissue of the abdominal wall, upper arm, thigh, the peritoneal cavity or the like.

The container 14 is formed with a pair of flanges 38 which extend diametrically outwardly from the upper end of the container. An elongated rod 40, having a cross section substantially less than the cross section of the passage 42 through the container 14, is arranged with a portion extending in telescoping relation through the open upper end 16 of the container. The rod 40 is formed through a substantial portion of its length, and preferably along its midsection, with external screw threads 44. The telescoping lower end portion of the rod 40 engages a piston member 46 having at least one, and preferably two or more, annular flanges 48 extending outwardly into sealing engagement with the inner wall of the container. The upper end portion of the rod 40, which projects beyond the open end 16 of the container 14, is provided with a transversely extending member or alignment pin 50 that engages a sleeve or drive tube 52, which will be described in greater detail with particular reference to FIGS. 8-13.

The rod 40 is adapted to be displaced axially into and out of the container 14 in response to the turning movement of the rod in one direction or the other. For this purpose, and for mounting the rod within the assembly, an operating member 54 is provided which is adapted to be removably mounted on the upper end of the container with an opening 56 in axial alignment with the container. The opening 56 includes screw threads 58 for threaded engagement with the threaded rod 40. The means mounting the operating member 54 is adapted to prevent rotational movement of the adaptor when in the assembled relation so that the piston 46 and rod 40 can be displaced axially relative to the container in response to the turning movement of the rod, as previously described. For this purpose, the operating member 54 includes a pair of flanges 60 which extend laterally for a distance slightly greater than that of the flanges 38 from the upper end of the container with a recessed portion 62 facing inwardly from the opposite ends for receipt of the flanges 38. In this manner, the operating member is secured to the upper end of the container to prevent the inadvertent turning movement of the operating member relative to the container 14, as illustrated in FIGS. 4 and 5 of the drawings.

The operating member 54 can be disengaged from the container 14 to enable removal of the operating member and its threadably engaged rod 40 and piston member 46 by turning the operating member relative to the container until the flanges 38 of the container clear the recessed portion 62 of the operating member, as shown by broken lines in FIG. 4 of the drawings.

Referring again to FIG. 3, the piston member 46 is in the form of a hollow cylindrical section and is suspended from the lower end of the rod 40 by means of a disc member 64 dimensioned to have a length less than the length and a dimeter slightly less than the diameter of the hollow section, but having a diameter greater than that of a passage 66 through which a pin 68 extends from the lower end of the rod 40. The disc member 64 is secured to the through extending portion of the pin. Thus the disc member 64 is slidably located within the cylindrical section of the piston member 46 for axial displacement of the piston in response to axial movement of the rod 40 while being free to enable turning movement of the rod without a corresponding movement of the piston.

The portion of the rod 40 that extends beyond the top 16 of the container 14 is adapted to be enclosed by means of a tubular member 70 in the form of a cover having an interior passage of greater diameter than the rod. The tubular member 70 is also adapted to have a length greater than the portion of the rod 40 that extends beyond the operating member 54. Moreover, the tubular member is closed at its upper end 72 and is adapted at its lower end to pressfit about a cylindrical section 74 formed upwardly from the top wall of the operating member 54. The cover is preferably provided with a clip 76 for releasably securing the device to the clothing of the user.

Referring again to FIG. 1, means is provided for controllably advancing the rod 40 and piston member 46 within the container 14 comprising the drive tube 52 concentrically mounted about the rod 40, the drive tube 52 having ramp means 80 at the upper end thereof, the ratchet head assembly 74 including at least one resilient member 82 in operative communication with the upper end 84 of the drive tube 52 and a rotatable knob 86 adjacent the ratchet head assembly 74 whereby rotation of the knob 86 in one direction rotates the drive tube 52 and the rod 40 to deliver the fluid through the outflow channel 18 of the container 14.

The drive tube 52 comprises a cylindrical portion 88, which can be slidably inserted within the tubular member 70, having at least one channel 90 extending longitudinally along the inner wall thereof to releasably engage the alignment pin 50 at the upper end of the rod 40. The alignment pin 50 can extend transversely from the rod in one direction (not shown) or from diametrically opposed sides of the rod (as illustrated). If the alignment pin 50 extends from opposed sides of the rod 40, the drive tube 52 includes a pair of diametrically opposed channels 90 for operative communication with the rod.

The upper end 84 of the drive tube 52 includes a portion 96 that has a narrowed diameter relative to the cylindrical portion 88. The top surface of the portion 96 comprises an annular platform 98 having a central passage 100 and a series of equidistant slots 102 formed therein. Between adjacent slots 102 is a sloped surface 104 that extends from near the lowermost point of one slot to the uppermost point of an adjacent slot (see FIGS. 9, 10 and 13).

The upper end 84 of the drive tube 52 is connected to the rotatable knob 86 by screw means 106 with the ratchet head assembly 74 held therebetween. Specifically, referring to FIG. 8, the upper portion of the device is detailed. The alignment pin 50 is shown mounted to an extension 108 at the upper end of the rod 40. The alignment pin 50 slidably engages the opposed channels 90 of the drive tube 52 which, in turn, is slidably inserted within the tubular member 70 (see FIG. 11).

Screw means 106 extends through the central passage 100 in the annular platform 98 of the drive tube and into a corresponding opening 110 in the knob 86. The knob includes a circular top portion 112 having a knurled or roughened surface along its circumference to facilitate gripping. Extending from the circular top portion 112 is a shaft member 114 that contains the opening 110 and can seat within a recessed portion 116 in the annular platform 98 of the drive tube concentric with the central passage 100.

Mounted between the knob 86 and the drive tube 52 is the ratchet head assembly 74 which is also cylindrical in shape, but which non-rotatably engages the upper portion of the tubular member 70. The upper edge of the ratchet head assembly includes an annular ring 118 which functions to seat the ratchet head assembly 74 between the knob 74 and the tubular member 70.

Referring to FIGS. 9-10 and 12, the construction and operation of the ratchet head assembly 74 can be better understood. In FIG. 12 the annular ring 118 of the ratchet head assembly 74 is shown. A central portion 120 of the assembly 74 includes at least one resilient member 82 integrally molded to the inner side wall of the assembly. In the illustrated embodiment, two resilient members 82 are included, each being arcuate shaped and including a body portion 122 and a tab portion 124 at the distal end 126 thereof. The central portion 120 also includes an opening 128 for receiving the shaft member 114 of the knob 86. The tab portions 124 extend at an angle from the body portions 122 and are adapted to engage the ramp means 80 at the upper end of the drive tube 52 when the device is assembled (see FIGS. 9 and 10).

FIG. 9 shows a resilient member 82 and the ramp means 80 in the released position for rotation of the drive tube 52 and, therefore, the rod 40 as the knob 86 is rotated to deliver a fluid through the outflow channel 18 of the container. Note the sloped surface 104 of the ramp means 80 which the tab member 124 has traversed.

One embodiment of the ramp means 80 is shown in FIG. 13. Four equally spaced slots 102 are provided in the annular platform 98. Between each pair of slots 102 is a sloped surface 104 that extends from near the lowermost point of one slot to the uppermost point of an adjacent slot.

That orientation is also shown in FIG. 10 which illustrates the tab portion 124 of the resilient member 122 within a slot 102 to lock the circular motion of the drive tube 52 relative to the knob 86. The torque needed to enable rotation of the drive tube 52 upon rotation of the knob 86 is provided by tightening the screw means 106. Thus, the pressure exerted by the resilient member 122 on the ramp means 80 can be controlled.

It will be understood that the ramp means 80 can include any number of slots and sloped surfaces, but the components should be equally spaced to provide a uniform measure of the rotation of the drive tube 52 and rod 40. Moreover, the direction of the incline of the sloped surfaces 104 determines the direction that the knob 86 is rotated to deliver the fluid. The knob will, of course, rotate in the opposite direction but in so doing will not advance the rod. When the knob is being rotated in the proper direction, a click is produced as the tab portions 124 engage the slots 102. This permits use of the device to deliver a predetermined volume of fluid without direct viewing of the device.

In use, with the fluid to be infused or injected filling the space within the container 14, the outflow channel 18, the tubing 34 and the needle 36, the patient inserts the needle, and then rotates the knob 80. The volume of fluid expelled from the container 14 and infused into the patient per revolution of the rod 40 is predetermined. For example, if insulin is the fluid, a thread size can be selected so that each revolution of the knob delivers precisely four units of U-100 insulin. The term U-100 indicates 100 units of insulin per milliliter of solution. As discussed, when the tab portion 124 of the resilient member 82 engages a slot 102, a distinct click can be heard which indicates that the rod has been rotated through $\frac{1}{4}$ turn and, therefore, one unit of insulin has been delivered. Other thread sizes, of course, can also be used.

When the fluid 12 is to be infused as a suspension, efficient mixing of the fluid particulates is fundamental to the safe operation of the device. Before a volume of fluid is delivered, the particulate matter in the fluid 12 must be resuspended by inverting the device several times from end to end. Referring back to FIG. 3, a metal ball 126 can be provided in the container 14 to facilitate mixing of the fluid. The ball 126 functions to prevent the particles in the fluid 12 from sedimenting through the outflow channel 18 of the container 14, and down the outflow channel.

FIG. 6 illustrates a modification wherein means are provided to collect sedimenting particles other than over the container outflow to prevent a significant amount of these particles from sedimenting through the container outlet. Specifically, an annular lip 128 extends upwardly from the bottom wall of the container 14 about a passage 120 so that the diameter of the lip is less than the inner diameter of the container, preferably 0.090 inches or less, thereby to provide an annular space 132 that functions as a well into which any sedimenting particles are collected for resuspension. Agitation with an air pocket upon repeated inversion of the device is performed before the next injection or infusion to resuspend the particles. The inner wall of the container includes an annular ledge 134 to engage the piston member 46 at the completion of the downward stroke of the rod 40. As a result, the piston member 46 does not contact the annular lip 128 so that the lip is not bent or otherwise deformed by operation of the rod.

Referring now to FIG. 7, an additional modification is shown in the lower end of the container 14 to prevent loss of insulin crystals through sedimentation. A needle 136 sealably engages the passage 130, while the upper end 136 of the needle extends well into the lower portion of the container. In this manner, an annular space 140 is formed in the container bottom for the collection of sedimented particles which can be resuspended by an air pocket upon repeated inversion of the device. The piston member 46 includes a cutaway section 142 which receives the upper end 138 of the needle and prevents damage to the needle as the rod 40 and piston member are moved downwardly through the container 14. In this manner, the needle 136 is not deformed during the downward stroke of the rod. The needle 136, preferably with an inner diameter of 0.090 inches or less, can be pressfit or thermosealed within the passage 130 and is protected by a removable cap 144 which maintains sterility and protects the sharp cutting point used for subcutaneous injections when the device is not in use.

The embodiment of FIG. 7 can be used for multiple daily injections of the insulin mixture. Consequently, a patient can carry a one to three day supply of insulin in a single syringe and avoid the necessity of carrying multiple disposable syringes, needles and vials of insulin. In addition, the patient need not be connected to a continuous infusion device between infusions.

To use the device in the administration of insulin to a diabetic patient, for example, a mixture of short-acting regular insulin and a long-acting crystalline insulin is added to the device through the outflow channel 18. A sufficient volume is used so that the container 14 holds at least a 24 hour supply of insulin. The adaptor 16 and tubing 32 are connected and filled with insulin; thereafter, the needle 34 is inserted subcutaneously. After the insertion of the needle tape means 36 is secured to the needle. The tape means can comprise adhesive tape, or what is commonly referred to as a "butterfly", suitable for attachment to the skin. Preferably, however, the tape means 36 comprises a flexible mounting plate 146 having two adjacent ridges 148 formed thereon to define a channel 150. The channel is adapted to removably receive the needle 136 and to mount the needle in a stationary position during use.

In preferred practice, the needle is slightly bent as shown in FIG. 1 to minimize tissue damage if the needle should move or rotate after insertion. Movement of the needle after subcutaneous insertion would produce tissue damage as the needle tip slices the skin and widens the needle track; viz., the passage formed between the needle and the skin of the patient as the needle is inserted into the skin. A bent or curved needle decreased this damage. The mounting plate 146 can, of course, be secured to the skin by tape or can be self-adhesive. The use of an adhesive mounting plate and the bent needle has been found to be superior to conventional means for subcutaneous infusion. The container, piston, adaptor, tubing, mounting plate and needle are disposable and, along with the infusion site, should be changed every one to three days.

The administration of four bolus infusions per day, specifically one infusion before each meal and one before the bed time snack, is adequate to maintain a relatively constant blood glucose level in the diabetic patient. The regular insulin acts rapidly to metabolize the carbohydrates ingested at each meal, and the ultralente insulin maintains a baseline insulin level in the blood for longer periods of time. Such premeal and presnack administration of insulin has the effect of simulating the release of insulin by the pancreas and thereby normalizing blood glucose levels in the diabetic. The device can be used in a like manner to deliver any medication to a patient.

It will be understood that various changes and modifications can be made in the above described apparatus without departing from the spirit thereof, particularly as defined in the following claims.

That which is claimed is:

1. A device for the infusion of measured amounts of a fluid comprising:
    (a) a container having an outlet opening at a first end and an opening at a second end;
    (b) fluid displacement means operating in the container for the displacement of measured amounts of fluid from the container through the outlet opening at the first end, including an elongate rod extending into the container through the opening at the second end and having a piston head in sealing engagement with the container for displacement of fluid from the container through said outlet opening in response to displacement of the piston head and rod relative to the container in the direction towards the first end of the container;
    (c) means for endwise displacement of the piston and rod comprising a threaded portion on the length of the rod and an operating member fixed on the container in threaded engagement with the threaded portion of the rod; and
    (d) means for controllably advancing the elongate rod within the container comprising an elongate sleeve concentrically mounted over said rod for conjoint rotation with said rod having ramp means at the upper end thereof, a resilient member rotatable about the longitudinal axis of said elongate sleeve in operative communication with said ramp means and actuating means connected to said elongate sleeve with said resilient member being immovably held therebetween;

whereby rotation of said actuating means rotates the elongate sleeve and the rod to displace the fluid through the outlet opening at said first end of the container.

2. A device as claimed in claim 1 in which the container comprises a hollow tubular member open at both an upper end and a lower end and includes a flange at the upper end extending outwardly for a distance greater than the diameter of the container.

3. A device as claimed in claim 1 in which said operating member includes a channel on its lower surface and said hollow tubular member includes a flange at the upper end of the container to lock the lower portion of the rod in a secure relationship within the container.

4. A device as claimed in claim 1 wherein said elongate rod includes a pin extending transversely relative to the longitudinal axis of the rod and said elongate sleeve includes at least one groove extending parallel to the longitudinal axis of the sleeve so that when the sleeve is concentrically mounted over said rod for conjoint rotation, the pin engages the sleeve for slidable movement within said groove.

5. A device as claimed in claim 1 wherein said ramp means comprises at least one radially extending slot and at least one sloped surface in the upper surface of said sleeve for operative engagement with said resilient member.

6. A device as claimed in claim 1 wherein said resilient member comprises a cylindrical member having a resilient body portion extending therefrom, said body portion including a tab portion at one end for operatively engaging said ramp means to control the rotational movement of said elongate sleeve 7. A device as claimed in claim 1 further including means for stopping the displacement of the piston head and the rod relative to the container in the direction towards the first end of the container before the piston head engages the outlet opening at the first end of the container.

8. A device as claimed in claim 7 further including means at the outlet opening of the container for militating against sedimentation of any solid particles, which might be present in the fluid, through the outlet opening and blockage of the outlet opening by the accumulation of the particles from the fluid.

9. A device as claimed in claim 8 in which the means at the outlet opening comprises a sphere of substantially greater density than the fluid and which settles over the outlet opening to block the sedimentation of insulin crystals through said outlet opening.

10. A device as claimed in claim 8 in which the means at the outlet opening comprises an annular lip on the inner wall of the container extending upwardly from the lower end thereof.

11. A device as claimed in claim 8 in which the means at the outlet opening comprises a needle sealably engaging said outlet opening, the upper portion of the needle extending into the container to form an annular space for the accumulation of sediment from the fluid, and the lower end made suitable for subcutaneous injection directly or through a catheter connected to a needle.

12. A device as claimed in claim 10 or claim 11 in which said stopping means comprises an annular ledge in the inner wall of the container adjacent the first end thereof whereby the displacement of the piston head and the rod can be arrested before the piston head engages the outlet opening at said first end of the container.

13. A device as claimed in claim 10 in which said stopping means includes a cutaway section in the plunger head for receiving the annular lip that extends upwardly from the lower end of the inner wall of the container whereby the displacement of the piston head and the rod can be arrested before the piston head contacts the annular lip.

14. A device as claimed in claim 11 in which said stopping means includes a cutaway section in the plunger head for receiving the upper portion of the needle that extends upwardly into the container whereby the displacement of the piston head and the rod can be arrested before the piston head contacts the upper end of the needle.

15. A device as claimed in claim 1 which includes means for releasably enclosing the portion of the rod extending beyond the container and the sleeve to prevent inadvertent turning movement of the rod and the sleeve and the inadvertent loss of control in displacement of fluid.

16. A device as claimed in claim 15 in which the enclosing means comprises a tubular member dimensioned to have a length and diameter greater than the sleeve with means for releasably sealing the tubular member to the operating member.

17. A device as in claim 1 in which the rod has a small diameter relative to the container for preventing contact of said rod with the inner wall of the container.

18. A device as in claim 6 further including means within the container for aiding in the resuspension of said solid particles in the fluid upon inversion of the container before the displacement of the fluid from the container.

19. A device as in claim 18 in which said resuspension means is the sphere of substantially greater density than the surrounding fluid which settles to the bottom of the container upon inversion of the container.

20. A device as in claim 18 in which said resuspension means is an air pocket which rises in the container to resuspend the crystals upon inversion of the container.

21. A device as claim in claim 1 further including a needle for subcutaneous injection connected by tubing to the outlet opening of said container and tape means comprising a mounting plate having ridges thereon to form a channel for holding the needle in a stationary position during use.

22. A device as claimed in claim 21 in which the needle is bent to decrease tissue damage upon movement of the needle and the mounting plate is self-adhesive.

* * * * *